US006268547B1

(12) United States Patent
Weeks

(10) Patent No.: US 6,268,547 B1
(45) Date of Patent: Jul. 31, 2001

(54) TRANSFORMATION OF WHEAT WITH THE CYANAMIDE HYDRATASE GENE

(75) Inventor: James Troy Weeks, Lincoln, NE (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/518,988

(22) Filed: Mar. 3, 2000

Related U.S. Application Data

(62) Division of application No. 08/873,001, filed on Jun. 11, 1997, now abandoned.

(51) Int. Cl.⁷ .............................. C07H 21/04; C07K 1/00; C07K 14/00; C07K 17/00; A01H 1/00; A01H 5/00; C12N 5/00; C12N 5/02; C12N 5/04; C12N 5/10; C12N 9/00; C12N 15/00; C12N 15/09; C12N 15/63; C12N 15/70; C12N 15/74; C12N 15/82; C12N 15/87

(52) U.S. Cl. ..................... 800/288; 435/183; 435/410; 435/419; 435/320.1; 530/350; 536/23.2; 536/23.74; 800/278; 800/293; 800/300

(58) Field of Search ............................. 435/183, 410, 435/419, 320.1; 530/350; 536/23.2, 23.74; 800/278, 288, 293, 300

(56) References Cited

U.S. PATENT DOCUMENTS

| | | | |
|---|---|---|---|
| 5,023,179 | 6/1991 | Lam et al. | 435/172.3 |
| 5,367,110 | 11/1994 | Galili et al. | 800/205 |
| 5,405,765 | 4/1995 | Vasil et al. | 435/172.3 |
| 5,631,152 | 5/1997 | Fry et al. | 435/172.3 |
| 6,096,947 | 8/2000 | Jayne et al. . | |

FOREIGN PATENT DOCUMENTS 9848023   10/1998   (WO) .............................. C12N/15/60

OTHER PUBLICATIONS

D. Bradley, "Genetic Weeding and Feeding for Tobacco Plants," *New Scientist* p. 11 (Jan. 4, 1992).
J.T. Weeks, O. Anderson and A. Blechl, "Rapid Production of Multiple Independent Lines of Fertile Transgenic Wheat (*Triticum aestivum*)," *Plant Physiol.* 102:1077–1084 (1993).
J.P.A. Ortiz et al., Hygromycin Resistance as an Efficient Selectable Marker for Wheat Stable Transformation, *Plant Cell Reports* (15:877–881 (1996).
N.S. Nehra et al., "Self–fertile Transgenic Wheat Plants Regenerated from Isolated Scutellar Tissues Following Microprojectile Bombardment with Two Distinct Gene Constructs," *The Plant Journal* 5(2):285–297 (1994).
D. McElroy, W. Zhang, J. Cao, and R. Wu, "Isolation of an Efficient Actin Promoter for Use in Rice Transformation," *The Plant Cell* 2:163–171 (1990).

W. Zhang and R. Wu, "Efficient Regeneration of Transgenic Plants from Rice Protoplasts and Correctly Regulated Expression of the Foreign Gene in the Plants," *Theor. Appl. Genet.* 76:835–840 (1988).
R.M. Hauptmann et al., "Evaluation of Selectable Markers for Obtaining Stable Transformants in the Gramineae," *Plant Physiol.* 86:602–606 (1988).
G. Rieder, "Calcium cyanamide—Fertilizer or Pesticide?," *World Crops* pp. 17–22 (Jan. 1981).
U.H. Maier–Greiner et al., "Isolation and Properties of a Nitrile Hydratase from the Soil Fungus *Myrothecium Verrucaria* That Is Highly Specific for the Fertilizer Cyanamide and Cloning of its Gene," *Proc. Natl. Acad. Sci.* 88:4260–4264 (1991).
A. Wilmink and J.J.M. Dons, "Selective Agents and Marker Genes for Use in Transformation of Monocotyledonous Plants," *Plant Molecular Biology Reporter* (11(2):165–185 (1993).
U.H. Maier–Greiner et al., "Herbicide Resistance in Transgenic Plants through Degradation of the Phytotoxin to Urea," *Angew. Chem. Int. Ed. Engl.* 30(10):1314–1315 (1991).
A.H. Christensen, R.A. Sharrock and P.H. Quail, "Maize Polyubiquitin Genes: Structure, Thermal Perturbation of Expression and Transcript Splicing, and Promoter Activity Following Transfer to Protoplasts by Electroporation," *Plant Molecular Biology* 18:675–689 (1992).
H. Zhou et al., "Glyphosate–tolerant CP4 and GOX Genes as a Selectable Marker in Wheat Transformation," *Plant Cell Reports* 15:159–163 (1995).
K.A. Torbert, H.W. Rines, and D.A. Somers, "Use of Paromomycin as a Selective Agent for Oat Transformation," *Plant Cell Reports* 14:635–640 (1995).
A. Perl, S. Galili, O. Shaul, I. Ben–Tzvi and G. Galili, "Bacterial Dihydrodipicolinate Synthase and Desensitized Aspartate Kinase: Two Novel Selectable Markers for Plant Transformation," *Bio/Technology* 11:715 (1993).
M.B. Hayford et al., "Development of a Plant Transformation Selection System Based on Expression of Genes Encoding Gentamicin Acetyltransferases," *Plant Physiol.* 86:1216–1222 (1988).
P.A. Lazzeri and P.R. Shewry, "Biotechnology of Cereals," *Biotechnology and Genetic Engineering Reviews*, Ed. M.P. Tombs, 11:79ff (Dec. 1993).
H. Ebinuma et al., "Selection of Marker–Free Transgenic Plants Using the Isopentenyl Transferase Gene," *Proc. Natl. Acad. Sci.* 94:2117–2121 (1997).

Primary Examiner—Phuong T. Bui
Assistant Examiner—Cynthia Collins
(74) Attorney, Agent, or Firm—Margaret A. Connor; Nancy J. Parsons; M. Howard Silverstein

(57) ABSTRACT

Methods of genetic transformation of plants utilizing the cyanamide hydratase gene as a selectable marker are disclosed. Methods of producing fertile plants which have the ability to convert cyanamide into a nitrogen source are described.

9 Claims, 2 Drawing Sheets

SEQUENCE LISTING

```
(1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 1235 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: MYROTHECIUM VERRUCARIA (ix) FEATURE:
        (A) NAME/KEY: exon
```

(B) LOCATION: 281..500

(ix) FEATURE:
            (A) NAME/KEY: exon
            (B) LOCATION: 564..1078

(ix) FEATURE:
            (A) NAME/KEY: CDS
            (B) LOCATION: join(281..500, 564..1078)
            (D) OTHER INFORMATION: /EC_number= 4.2.1.69
                /product= "cyanamide hydratase"
                /citation= ([1])

(x) PUBLICATION INFORMATION:
            (A) AUTHORS: MAIER-GREINER, URSULA H.
                         OBERMAIER-SKROBRANEK, BRIGITTE M.
                         ESTERMAIER, LYDIA M.
                         KAMMERLOHER, WERNER
                         FREUND, CHRISTIAN
                         WULFING, CHRISTOPH
                         BURKERT, ULRIKE I.
                         MATERN, DAGMAR H.
                         BREUER, MICHAEL
                         EULITZ, MANFRED
            (B) TITLE: ISOLATION AND PROPERTIES OF A NITRILE
                HYDRATASE FROM THE SOIL FUNGUS MYROTHECIUM
                VERRUCARIA THAT IS HIGHLY SPECIFIC FOR THE
                FERTILIZER CYANAMIDE AND CLONING OF ITS GENE
            (C) JOURNAL: Proc. Natl. Acad. Sci. U.S.A.
            (D) VOLUME: 88
            (F) PAGES: 4260-4264
            (G) DATE: MAY-1991
            (K) RELEVANT RESIDUES IN SEQ ID NO: 1: FROM 1 TO 1235

(xi) SEQUENCE DESCRIPTION: SEQ ID NO: 1:

```
CGGCTCTTAT ACGACATTGA TTAGAAATGC AATTGACGCA AAATGGAAGT TATACGACAA      60

GCGCAATAAT GGATTGAGCA CTTATCGAAC ACGTACGTCA TAGTGAACAT TGGCCACTGT     120

TGTCTCTGGT CCCCTCAAAC GTATAACCCT TATTGAGGAC TTGGGTATAT ATACACGCAC     180

TATCCGTCAT GTTTCACGAA AGGTCGACCT CATACTCCTA CGTTTCTCAA ACTAGTACGA     240

TCCTACTTCC TCGCTTATCT GCTCTAAACG ATTCAACAAG ATG TCT TCT TCA GAA       295
                                             Met Ser Ser Ser Glu
                                               1               5

GTC AAA GCC AAC GGA TGG ACT GCC GTT CCA GTC AGC GCA AAG GCC ATT       343
Val Lys Ala Asn Gly Trp Thr Ala Val Pro Val Ser Ala Lys Ala Ile
             10                  15                  20

GTT GAC TCC CTG GGA AAG CTT GGT GAT GTC TCC TCA TAT TCT GTG GAA       391
Val Asp Ser Leu Gly Lys Leu Gly Asp Val Ser Ser Tyr Ser Val Glu
         25                  30                  35

GAT ATC GCG TTC CCT GCG GCA GAC AAA CTT GTT GCC GAG GCA CAG GCC       439
Asp Ile Ala Phe Pro Ala Ala Asp Lys Leu Val Ala Glu Ala Gln Ala
     40                  45                  50

TTT GTG AAG GCC CGA TTG AGT CCC GAA ACC TAC AAT CAC TCC ATG CGC       487
Phe Val Lys Ala Arg Leu Ser Pro Glu Thr Tyr Asn His Ser Met Arg
 55                  60                  65

GTT TTC TAC TGG  G GTAAGTCATG CCGTGCTGCG TGCCTGACAT AATTCCAAAT        540
Val Phe Tyr Trp
 70

TCTCACAAAT ATTTTCCAAC AAG  GA ACC GTC ATC GCG AGA CGT TTA CTT         589
                          Gly Thr Val Ile Ala Arg Arg Leu Leu
                                   75                  80

CCC GAG CAA GCT AAA GAC TTG TCT CCA AGT ACA TGG GCA CTG ACA TGT       637
Pro Glu Gln Ala Lys Asp Leu Ser Pro Ser Thr Trp Ala Leu Thr Cys
             85                  90                  95

CTT CTG CAT GAC GTT GGT ACT GCG GAG GCA TAC TTT ACA TCT ACA CGA       685
Leu Leu His Asp Val Gly Thr Ala Glu Ala Tyr Phe Thr Ser Thr Arg
        100                 105                 110
```

-continued

```
ATG TCC TTC GAT ATT TAC GGT GGC ATT AAG GCT ATG GAG GTG CTC AAG      733
Met Ser Phe Asp Ile Tyr Gly Gly Ile Lys Ala Met Glu Val Leu Lys
115             120                 125                 130

GTC CTT GGG AGT AGC ACC GAC CAG GCT GAG GCT GTT GCC GAG GCC ATC      781
Val Leu Gly Ser Ser Thr Asp Gln Ala Glu Ala Val Ala Glu Ala Ile
                135                 140                 145

ATT CGT CAT GAG GAT GTG GGG GTA GAT GGC AAC ATC ACA TTC CTC GGT      829
Ile Arg His Glu Asp Val Gly Val Asp Gly Asn Ile Thr Phe Leu Gly
            150                 155                 160

CAG TTG ATC CAG CTG GCT ACG CTT TAT GAC AAT GTC GGG GCC TAC GAT      877
Gln Leu Ile Gln Leu Ala Thr Leu Tyr Asp Asn Val Gly Ala Tyr Asp
        165                 170                 175

GGG ATT GAT GAT TTT GGT AGC TGG GTT GAT GAC ACC ACA CGC AAC AGT      925
Gly Ile Asp Asp Phe Gly Ser Trp Val Asp Asp Thr Thr Arg Asn Ser
    180                 185                 190

ATC AAC ACG GCA TTC CCA CGA CAT GGT TGG TGT TCT TGG TTT GCC TGC      973
Ile Asn Thr Ala Phe Pro Arg His Gly Trp Cys Ser Trp Phe Ala Cys
195                 200                 205                 210

ACG GTT CGT AAG GAA GAA AGT AAC AAG CCT TGG TGC CAC ACA ACG CAT     1021
Thr Val Arg Lys Glu Glu Ser Asn Lys Pro Trp Cys His Thr Thr His
                215                 220                 225

ATC CCT CAG TTC GAT AAA CAG ATG GAA GCG AAC ACT TTG ATG AAG CCT     1069
Ile Pro Gln Phe Asp Lys Gln Met Glu Ala Asn Thr Leu Met Lys Pro
            230                 235                 240

TGG GAG TAACTCTGAG TAAGCAGAGA ATATTTAGCC GGGTAGCTAT AGATGAATCT      1125
Trp Glu
        245

GGACAAATTC AGGCACATTT GGTTTCACGA TACAGGTATT GGAAATAGCT TGCAGGAAGG   1185

TATCATGTCA ACACCATGTA TTTTATTTTC CCTCGGTGAT TTAAATGGGG              1235
```

(2) INFORMATION FOR SEQ ID NO: 2:

(i) SEQUENCE CHARACTERISTICS:
        (A) LENGTH: 244 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Ser Glu Val Lys Ala Asn Gly Trp Thr Ala Val Pro Val
1               5                   10                  15

Ser Ala Lys Ala Ile Val Asp Ser Leu Gly Lys Leu Gly Asp Val Ser
                20                  25                  30

Ser Tyr Ser Val Glu Asp Ile Ala Phe Pro Ala Asp Lys Leu Val
            35                  40                  45

Ala Glu Ala Gln Ala Phe Val Lys Ala Arg Leu Ser Pro Glu Thr Tyr
        50                  55                  60

Asn His Ser Met Arg Val Phe Tyr Trp Gly Thr Val Ile Ala Arg Arg
65                  70                  75                  80

Leu Leu Pro Glu Gln Ala Lys Asp Leu Ser Pro Ser Thr Trp Ala Leu
                85                  90                  95

Thr Cys Leu Leu His Asp Val Gly Thr Ala Glu Ala Tyr Phe Thr Ser
            100                 105                 110

Thr Arg Met Ser Phe Asp Ile Tyr Gly Gly Ile Lys Ala Met Glu Val
        115                 120                 125

Leu Lys Val Leu Gly Ser Ser Thr Asp Gln Ala Glu Ala Val Ala Glu
    130                 135                 140
```

-continued

```
Ala Ile Ile Arg His Glu Asp Val Gly Val Asp Gly Asn Ile Thr Phe
145                 150                 155                 160

Leu Gly Gln Leu Ile Gln Leu Ala Thr Leu Tyr Asp Asn Val Gly Ala
                165                 170                 175

Tyr Asp Gly Ile Asp Asp Phe Gly Ser Trp Val Asp Asp Thr Thr Arg
                180                 185                 190

Asn Ser Ile Asn Thr Ala Phe Pro Arg His Gly Trp Cys Ser Trp Phe
            195                 200                 205

Ala Cys Thr Val Arg Lys Glu Glu Ser Asn Lys Pro Trp Cys His Thr
        210                 215                 220

Thr His Ile Pro Gln Phe Asp Lys Gln Met Glu Ala Asn Thr Leu Met
225                 230                 235                 240

Lys Pro Trp Glu
```

TRANSFORMATION OF WHEAT WITH THE CYANAMIDE HYDRATASE GENE

CROSS-REFERENCE TO RELATED APPLICATIONS

This application is a division of U.S. patent application Ser. No. 08/873,001, filed Jun. 11, 1997 now abandoned.

FIELD OF THE INVENTION

The present invention relates to the genetic transformation of monocotyledonous plants such as wheat, to methods of selecting stable genetic transformants, and to methods of producing fertile plants from the transformed cells. The selection method involves using the cyanamide hydratase gene from a soil fungus as a selectable marker. In addition to providing a means of selecting transformants, the cyanamide hydratase gene gives the plant the ability to convert cyanamide into urea as a fertilizer source. In other aspects, the invention relates to the production of stably transformed and fertile monocotyledonous plants, gametes, seeds and offspring from the transgenic plants.

BACKGROUND OF THE INVENTION

Wheat cultivation began somewhere in the middle east and has been ongoing for perhaps as long as 10,000 years. Today, wheat, rice and maize form the foundation of the human diet in every corner of the world. Of these three, wheat is the most widely grown and is the single greatest source of dietary protein in the human diet.

The importance of wheat and the other cereals, both because they are favorites for human consumption and because of their economic value, have led to their prominence in visions of the future of biotechnology. The full impact of biotechnology on agriculture will occur only when all the necessary technologies are available to cereal scientists, a prerequisite that is yet to be fulfilled. There are many aspects to biotechnological approaches to wheat modification, but the technical requirements can be divided into two basic categories. The first is transformation; i.e., there must be protocols to introduce exogenous genes directly into the wheat genome. Once this DNA is integrated into the wheat genome, it must be stable and passed on to the subsequent generations. Without this technology, the full power of molecular biology cannot be applied to this critical crop. The transformation protocols must be efficient and accessible to many laboratories. In spite of wheat's importance, research and development must balance the significance of the crop under study with the technical ease of manipulation. The second requirement for bioengineering wheat is the possession of genes that researchers have a reasonable expectation will confer positive traits if these genes can be transformed into wheat. Such genes will include those affecting herbicide resistance, insect and viral resistance, storage proteins, and starch metabolism.

Many of the recent advances in plant science have resulted from application of the analytical power of recombinant DNA technology coupled with plant transformation. These approaches facilitate studies of the effects of specific gene alterations on plant development and physiology. They also make possible the direct manipulation of genes to bioengineer improved plant varieties. Although wheat (*Triticum aestivum*) is the largest crop in the world in terms of production, it was the last among economically important cereals to be transformed. Transformation of monocotyledonous plants, including cereals, has proven much more difficult than dicotyledonous plants, such as tobacco. No proof of transgenic cereal plants has been shown using viral vectors, incubation of dry seeds or embryos in DNA, liposome fusion with tissues and protoplasts, liposome injection, microinjection or electroporation. Vasil et al. (Bio/Technology 9:743–747, 1991) produced stably transformed wheat suspension-cell cultures from which they were unable to regenerate plants. Later, Vasil et al. (Bio/Technology 10:667–674, 1992) obtained several transformed callus lines after microprojectile bombardment of embryogenic callus and selection with the herbicide Basta. Transformed wheat plants were regenerated from one of these lines. These plants were unable to self-fertilize, but progeny could be produced by outcrossing to either wild-type pollen or ova. Although the work of Vasil and collaborators was a landmark in efforts to develop wheat transformation, the protocol they reported was limited in its utility by its dependence on the identification and establishment of a specific callus type in long-term tissue cultures.

A rapid and efficient method of producing transgenic wheat lines has been achieved (Weeks et al., Plant Physiol. 102:1077–1084, 1993). Callus tissue produced by immature embryos shortly after excision and culturing is the target for microprojectile-mediated DNA delivery. The callus tissue can be maintained and regenerated into fertile plants with high frequency. This procedure makes it feasible for the first time to do promoter and protein expression studies. In addition it allows for the introduction of economically and agronomically important traits into wheat, such as disease resistance, insect resistance and seed quality.

Due to the often low transformation frequencies achieved in plants, especially wheat, selectable markers are very important in identifying the transformants. The most commonly used selectable markers are antibiotic resistance genes and herbicide resistance genes. These markers have several disadvantages. The presence and constitutive expression of antibiotic resistance genes, while critical for the selection of transformants, are of no benefit to the plant. The use of antibiotics for selection also raises questions of regulatory approval and public acceptance in addition to problems with natural resistance. Similar problems may be encountered with the use of herbicides. An additional disadvantage of using herbicide resistance genes as selectable markers is the risk of the gene being introduced into the target weeds by natural crosses between the weeds and crops. This is especially critical in sorghum and oats, which can naturally cross with weeds such as Johnson grass and wild oat, respectively. The commercial application of agricultural biotechnology relies on the discovery of selectable markers which do not have such disadvantages. Additionally, selection methods based on the use of two selectable markers on the same tissue require that more selectable markers be found.

A gene from the soil fungus *Myrothecium verrucaria*, the cah gene, coding for the enzyme cyanamide hydratase, has been isolated and characterized (Maier-Greiner et al., Proc. Natl. Acad. Sci. USA 88:4260–4264, 1991). This enzyme converts cyanamide into urea by catalyzing the addition of a water molecule. Cyanamide is used as a fertilizer in aqueous solution or in the form of its calcium salt. Calcium cyanamide as a fertilizer has the advantage that the product itself and its metabolites do not cause any environmental concern (Rieder, World Crops, January 1981, pp17–20). FIG. 1 shows the breakdown of calcium cyanamide in the soil. Calcium cyanamide has the following advantages over urea or ammonium nitrate-based fertilizers:

1. Calcium cyanamide nitrogen is released gradually, so the amount of nitrogen available to the plant roots is never in excess of plant needs.

2. Calcium cyanamide nitrogen provides a more efficient plant food because losses by leaching, run-off or dentrification are minimized.
3. Fertilizer application costs are lower through reduction in frequency of application.
4. There is no nitrate pollution of ground water, streams and lakes.

Calcium cyanamide also functions as a herbicide due to its metabolite cyanamide, which controls germinating weed seeds and weed seedlings. The use of calcium cyanamide has diminished over the years in favor of hormonetype weed killers, soil herbicides and other specific compounds, which can achieve a 100% weed kill. However, there is increasing concern about the impact such herbicides have on the environment. Calcium cyanamide is effective when weed infestation is low, and when used as a fertilizer, can reduce the need for specific herbicides. Another useful function of cyanamide is as a fungicide, especially for control of eye spot disease in wheat. Calcium cyanamide does not have the disadvantages of Benzimidazol fungicides, i.e., requiring correct timing and repeated applications and the problem of resistant strains. Calcium cyanamide has been shown to control foot rot diseases, leaf and ear diseases of small grains (Rieder 1981, supra).

Transgenic tobacco (*Nicotiana tabacum*) expressing the cah gene has been achieved (Maier-Greiner et al., Angew. Chem. Int. Ed. Engf. 30:1314–1315, 1991). The tobacco plants were infected with *Agrobacterium tumefaciens* containing a cah gene cassette, and the transformants were selected based on kanamycin resistance and regenerated. The transgenic tobacco plants were resistant to cyanamide and produced urea.

Zhou et al. (Plant Cell Reports 15:159–163, 1995) report the transformation of wheat using glyphosate-tolerant CP4 and GOX genes as a selectable marker. The CP4 and GOX genes were isolated from bacteria and confer resistance to glyphosate, which is the active ingredient in the non-selective herbicide Roundup (Monsanto Co.) The transformation efficiency for the CP4 and GOX genes was lower than that achieved using nptII (kanamycin resistance) or bar (glufosinate resistance) genes as selectable markers.

Ortiz et al. (Plant Cell Reports 15:877–881, 1996) report transformation of wheat using hygromycin resistance as a selectable marker. The hpt gene confers resistance to the antibiotic hygromycin. Ortiz et al. achieved an average transformation efficiency of 5.5% using the hpt gene, as compared to an efficiency of 2.6% for the bar-gene. The relatively high transformation efficiency was achieved in part due to the fact that the selection strategy did not attempt to eliminate all escapes. The escape rate was 5–10%.

SUMMARY OF THE INVENTION

The present invention is directed to an expression cassette encoding the cyanamide hydratase (cah) gene and methods of selecting stable genetic transformants, methods of providing a source of nitrogen and methods of conferring herbicide resistance to plants by introducing and expressing the cah gene. The cah gene functions as a selectable marker in plant transformation.

The invention further provides transgenic plant cells containing the cah gene according to the invention or transformed by an expression vector according to the invention, as well as transgenic plants expressing cyanamide hydratase regenerated from said plant cells, and tissues derived from said transgenic plants.

The expression cassette of the invention comprises a gene encoding cyanamide hydratase from the soil fungus *Myrothecium vernucaria* operably linked to a promoter functional in a plant cell. The expression cassette may also include genes for value added traits including insect resistance, disease resistance, and seed quality.

DETAILED DESCRIPTION OF THE INVENTION

One object of the invention is to produce plants exhibiting the ability to convert cyanamide first into urea and then into ammonia and having cyanamide resistance by transformation of plant cells with a recombinant DNA molecule comprising: (a) a DNA sequence coding for an enzyme having cyanamide hydratase activity, and (b) DNA sequences enabling expression of the enzyme in plant cells, thus giving the plant the ability to convert cyanamide into ammonia for a nitrogen source. In a preferred embodiment, the plants are monocotyledonous plants such as wheat.

The DNA sequence coding for an enzyme having cyanamide hydratase activity may be derived from any suitable source, e.g., from *Myrothecium verrucaria* or may be a synthetic gene. The instant invention encompasses the DNA sequence of cyanamide hydratase derived from *Myrothecium verucara* or any nucleotide sequence which encodes the amino acid sequence of the enzyme, or any nucleotide sequence encoding the enzyme in which one or more amino acid substitutions have been made that do not affect the functional properties of the encoded enzyme. In a preferred embodiment, the DNA sequence coding for a cyanamide hydratase enzyme used according to the invention is synthetic. The cloning and sequence of the cyanamide hydratase gene are described by Maier-Greiner et al., Proc. Natl. Acad. Sci. USA 88:4260–4264, 1991, whose contents are hereby incorporated by reference in their entirety. Highly homologous sequences which encode cyanamide hydratase are also encompassed by the instant invention.

The DNA sequences enabling expression of the cyanamide hydratase enzyme in plant cells include any promoters which function in the host cell. In a preferred embodiment, the promoters are those which function in monocotyledonous plants such as the rice actin Act1 promoter (McElroy, et al. 1990, The Plant Cell, 2:163–171), the maize alcohol dehydrogenase Adh1 promoter (Zhang, et al. 1988, Theor. Appl. Genet. 76:835–840), the maize ubiquitin Ubi1 promoter, and the cauliflower mosaic virus 35S promoter. The preferred promoter is the maize ubiquitin Ubi1 promoter, which is likely to be expressed in all plant tissues and has been shown to exhibit 10-fold higher activity than a similar construct containing the cauliflower mosaic virus 35S promoter (Christensen et al., supra).

Figure 1:
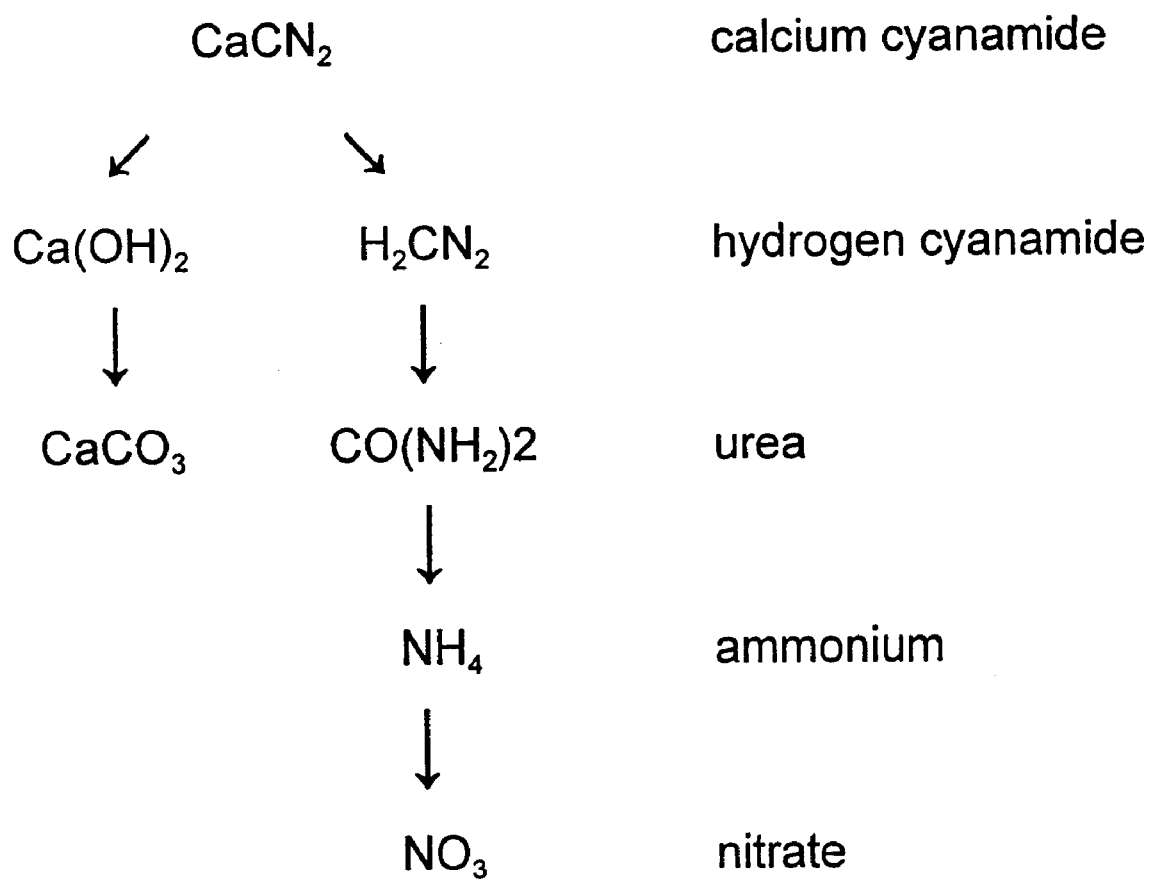
FIG. 1 shows the breakdown of calcium cyanamide in the soil.
Figure 2:
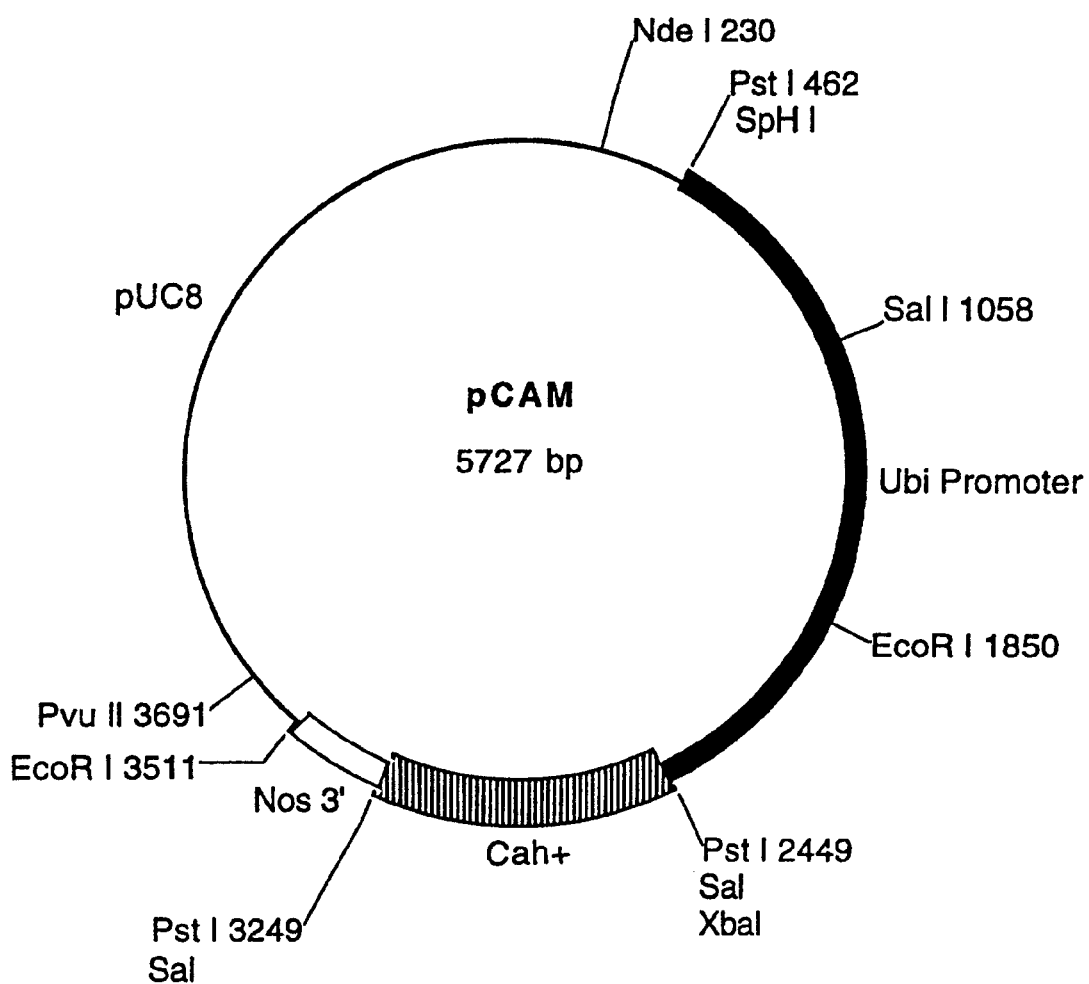
FIG. 2 shows the plasmid pCAM containing the cah gene and the Ubi1 promoter.

The pCAM plasmid was constructed by inserting the maize ubiquitin Ubi1 promoter, the cah gene, and the 3' termination sequences from the nopaline synthase (nos) gene into pUC8 (FIG. 2).

The expression vector comprising the cah gene is then introduced into plant cells. Any kind of transformation protocol capable of transferring DNA into plants can be used. Examples of such protocols include transformation by direct DNA transfer into plant cells by electroporation (Dekeyser, R. A. et al., 1990, The Plant Cell 2:591–602), PEG precipitation (Hayashimoto, A. et al., 1990, Plant Physiol. 93:857–863), infection with Agrobacterium (Horsch, R. B. et al. 1985, Science 227:1229–1231), microprojectile bombardment of embryogenic cells lines (Vasil et al. 1992 supra), cultured immature embryos (Weeks et al. supra) or scutellar embryogenic tissues (Nehra et al. Plant Journal 5:285–297, 1994). The preferred method is microprojectile bombardment of cultured immature embryos. The methodology described here for wheat can be applied to other plants such as maize, rice, sorghum and barley.

The method of selecting transformed plant tissue is based on resistance to cyanamide. Immature embryos are removed from wheat caryopses and cultured on maintenance media to form callus tissue. The callus tissue is bombarded with DNA-covered microprojectiles. After bombardment, the callus tissue is transferred to selection media containing cyanamide. When the embryogenic callus begins to proliferate, it is subcultured on regeneration media containing cyanamide. The resulting shoots are transferred to rooting media also containing cyanamide. Resistant transformed plants will continue to thrive and grow in the cyanamide-containing media. The transgenic plants produce cyanamide hydratase which converts the cyanamide in the media into urea, which the plant then converts to ammonia and utilizes as a nitrogen source.

A standard colorimetric assay was used to test the transgenic plants for cyanamide hydratase activity (Maier-Greiner 1991a and 1991b, supra). The assay is based on the decrease in cyanamide concentration during incubation with cyanamide hydratase. The cyanamide concentration was determined by a colorimetric assay at 530 nm. Cyanamide hydratase activity was found in all of the transgenic plants.

In another embodiment, the invention relates to the use of calcium cyanamide as a fertilizer and selective herbicide with the transgenic plants of the invention. Cyanamide is used as a fertilizer in aqueous solution or in the form of its calcium salt. Calcium cyanamide functions as a herbicide due to its metabolite cyanamide, which controls germinating weed seeds and weed seedlings. At the present time calcium cyanamide is not generally used in the United States as a herbicide because of the introduction of hormone-type weed killers, soil herbicides and other specific compounds, which can achieve a 100% weed kill. However, in light of the increasing concern about the impact such herbicides have on the environment, calcium cyanamide is an alternative because the product itself and its metabolites do not cause any environmental concern. Calcium cyanamide is effective when weed infestation is low, and when used as a fertilizer, can reduce the need for specific herbicides.

Thus, according to the invention, cyanamide can be used as a fertilizer and selective herbicide allowing weed control with only the transgenic crop plants being resistant. In this way crops can be protected from weeds and simultaneously fertilized with a chemical compound which is not detrimental to the environment.

EXAMPLES

Example 1

Target Tissue Establishment and Bombardment

Plant Material

Highly embryogenic callus tissue derived from wheat plants (*Triticum aestivum* L. em. Thell. cv Bobwhite) was used. To establish callus cultures caryopses 10 to 18 days post-anthesis were surface-sterilized with 70% ethanol for 5 minutes and 20% sodium hypochlorite for 15 minutes, followed by two changes of sterile distilled water. Immature embryos, 0.5 to 1 mm long, were aseptically removed using a sterilized 11 cm forceps in a laminar flow hood under a stereo dissecting microscope. The embryos were placed with the scutella exposed on Murashige and Skoog (MS) maintenance medium (Murashige and Skoog, Physiol Plant 15:473–497,1962, modified for wheat cell culture, Sears and Deckard, Crop Sci. 22:546–550, 1982) modified for wheat culture and solidified with 2.5 g/l Phytagel. Calli were maintained at 25° C. with a 16 hour photoperiod (43 $\mu E/m^2$) on MS medium with 20 g/l sucrose, 1.5 mg/l 2,4-D and transferred to new medium at 2-week intervals.

Transforming DNA

The vector used for wheat transformation consisted of the cah gene under the control of the maize ubiquitin Ubi1 promoter (Christensen et al., Plant Mol. Biol. 18:675–689, 1992). Plasmid DNA was purified from alkaline-lysed cells on CsCl gradients and stored at a concentration of 1 mg/ml in Tris-EDTA buffer, pH 8.0 (Sambrook et al., Molecular Cloning: A Laboratory Manual. Cold Spring Harbor Press, Cold Spring Harbor, N.Y., 1989).

Microprojectile Bombardment Preparation

Prior to bombardment, 1 $\mu$m gold particles were coated with transforming DNA by the procedure of Daines (Biolostic Systems Newsletter 1:1–4, 1990). A stock suspension of gold particles was suspended at 60 mg/ml in absolute ethanol. Thirty-five microliters of the suspension was transferred into a 1.5 ml microcentrifuge tube, centrifuged at 14,000 g for 3 minutes, and the pellet was suspended in 200 $\mu$l of sterile distilled water. Following a second centrifugation, the pellet was suspended in 25 $\mu$l of Tris-EDTA containing 25 $\mu$g of the transforming plasmid DNA. The following chilled sterile solutions were added in order: 220 $\mu$l of water, 250 $\mu$l of 2.5 M $CaCl_2$, and 50 $\mu$l of 0.1 M spermidine (0.2 $\mu$m filter-sterilized). The microcentrifuge tubes were shaken with a Tomy microtube shaker at 4° C. for 15 minutes and centrifuged at 16,000 g for 5 minutes. The supernatant was removed, and the pellet was washed with 200 $\mu$l of ethanol and the DNA-coated gold particles were suspended in 36 $\mu$l of ethanol.

Procedure

The immature embryos were removed from wheat caryopses and cultured on MS maintenance medium for 5 days. If the immature embryos are less than 0.5 mm they may die in culture and if they are larger than 1.0 mm they may precociously germinate instead of initiating into callus tissue.

Four hours prior to bombardment, approximately 50 embryo-derived calli were placed in a circle (4 cm in diameter) in the center of a Petri dish (15×100 mm) containing 0.4 M mannitol in MS maintenance medium solidified with 3.5 g Phytagel.

The Petri dish containing the target callus tissue was placed in the biolistic device and 10 $\mu$l of the DNA-gold suspension was pipetted onto the center of a macroprojectile. The distance between the stopping plate and the target callus tissue was adjusted to 13 cm. The callus tissue was bombarded under vacuum with the rupture disk strength at 1100 p.s.i..

Example 2

Selection of Callus Tissue and Regeneration of Transgenic Plants

Sixteen hours following bombardment, 35 calli were transferred onto a Petri dish (20×100 mm) containing MS selection medium (37.5 mg cyanamide/l maintenance medium) Calli were maintained at 25° C. with a 16 hour photoperiod (43 μE/m²) and transferred onto fresh MS selection medium at 2-week intervals.

After the second transfer, small green sectors of cells (embryogenic callus) were proliferating. The green sectors and surrounding callus mass were subcultured to MS regeneration medium without 2,4-D (0.5 mg dicamba and 37.5 mg cyanamide/l maintenance medium). During the following 3 weeks, multiple shoots were induced and arose from the green sectors.

When the shoots reached 2–3 cm in size, they were transferred using sterilized long forceps to culture tubes (25×150 mm) containing 18 mls of rooting media (half-strength MS maintenance medium without hormones and with 62.5 mg/l cyanamide). Resistant shoots developed long, highly branched roots in the rooting medium. Sensitive shoots stopped growing and only developed a few short lateral roots. Vegetative tissue of sensitive plantlets exhibited yellow necrosis and reduced vigor within 1 week, whereas resistant plantlets continued to thrive and grow in the cyanamide-containing rooting medium.

After 2 weeks, the plantlets with an established root system were carefully removed from the rooting medium and transferred into pots containing potting soil. The plants were acclimated in an environmental chamber (21° C., 16 hour photoperiod (300 μE/m²)) with high humidity (80–90%) for 2 weeks before being transferred to the greenhouse. The plants flowered 5–8 weeks after transfer to the greenhouse.

Example 3

Cyanamide Hydratase Colorimetric Assay

Two cyanamide resistant plants were tested for cyanamide hydratase activity. The assay is based on the decrease in cyanamide concentration during incubation in the presence of the cyanamide hydratase enzyme. Wheat leaf plant tissue was frozen in liquid nitrogen, homogenized using a mortar and pestle, eluted with 5 mM sodium phosphate buffer (pH 8), vortexed for five minutes, and then centrifuged at 10,000 rpm for five minutes. The supernatant was decanted and 0.5 mM cyanamide was added to the solution. The solution was incubated for twelve hours at 25° C. After twelve hours sodium carbonate buffer solution (pH 10.4) and a color reagent (4% solution of trisodium pentacyanoammineferroate) were added. The solution was incubated for ten minutes at room temperature in the dark. The presence of cyanamide hydratase was determined by measuring absorbance at 530 nm.

Enzyme activity was found in both plants (Table 1). As controls, plants were transformed with the cyanamide hydratase gene in the opposite orientation (antisense) and tested for cyanamide hydratase activity. No activity was found in the control plants.

TABLE 1

Cyanamide Hydratase Colorimetric Assay

| Plant Line | Absorbance (530 nm) |
| --- | --- |
| Control 1 | 1.006 |
| 1650 | 0.867 |
| Control 2 | 1.011 |
| 1722 | 0.621 |

While the present invention has been described in connection with the preferred embodiment thereof, it will be understood that many modifications will be readily apparent to those skilled in the art, and this application is intended to cover any adaptations or variations thereof. It is manifestly intended that this invention be limited only by the claims and equivalents thereof. All patents and publications described herein are hereby incorporated by reference.

I claim:

1. A method for producing a transgenic plant, comprising the steps:
   (a) culturing immature plant embryos to form callus tissue;
   (b) transforming said callus tissue by delivering DNA coding for cyanamide hydratase into the cells of said callus tissue;
   (c) selecting for cyanamide hydratase resistant cells by growing said transformed cells on media containing cyanamide; and
   (d) regenerating transgenic plants from said transformed plant cells.

2. The method of claim 1 wherein said plant is a monocotyledonous plant.

3. The method of claim 2 wherein said monocotyledonous plant is wheat.

4. A method for selecting a transformed plant cell, which comprises:
   (a) transforming a plant cell from tissue or callus with an expression cassette comprising a nucleotide coding sequence which encodes cyanamide hydratase operatively linked to a promoter functional in said cell whereby expression of said coding sequence confers resistance of said transformed plant cell to cyanamide; and
   (b) selecting a cyanamide-resistant plant cell which expresses cyanamide hydratase, by growing said cell in the presence of cyanamide in an amount sufficient to prevent growth of cells not transformed with said coding sequence and sufficient to permit growth of cyanamide-resistant cells.

5. The method of claim 4 wherein said nucleotide sequence encodes the amino acid sequence shown in SEQ ID NO:2.

6. The method of claim 4 wherein said plant cell is from a monocotyledonous plant.

7. The method of claim 6 wherein said monocotyledonous plant is wheat.

8. The method of claim 4 wherein said plant cell is a callus cell.

9. The method of claim 4 wherein said selecting is performed in tissue culture.

* * * * *